United States Patent
Ohishi

(10) Patent No.: US 8,467,498 B2
(45) Date of Patent: Jun. 18, 2013

(54) IMAGE DIAGNOSTIC APPARATUS, IMAGE PROCESSING APPARATUS, AND PROGRAM

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1542 days.

(21) Appl. No.: 11/676,828

(22) Filed: Feb. 20, 2007

(65) Prior Publication Data

US 2007/0195931 A1    Aug. 23, 2007

(30) Foreign Application Priority Data

Feb. 20, 2006 (JP) ................................. 2006-042759

(51) Int. Cl.
*H05G 1/64*    (2006.01)
*G06K 9/36*    (2006.01)

(52) U.S. Cl.
USPC ............................ 378/98.12; 378/42; 382/130

(58) Field of Classification Search
USPC .............. 378/42, 98.12, 98.9, 98.11; 382/130
See application file for complete search history.

(56) References Cited

U.S. PATENT DOCUMENTS

| | | | | |
|---|---|---|---|---|
| 4,802,093 A | * | 1/1989 | Ema | ................................. 378/1 |
| 4,870,692 A | * | 9/1989 | Zuiderveld et al. | ............ 382/107 |
| 5,463,668 A | * | 10/1995 | Kagaya | ......................... 378/98.2 |
| 5,630,414 A | * | 5/1997 | Horbaschek | .................. 600/428 |
| 5,647,360 A | | 7/1997 | Bani-Hashemi et al. | |
| 5,956,435 A | * | 9/1999 | Buzug et al. | .................. 382/283 |
| 6,052,476 A | * | 4/2000 | Qian et al. | ...................... 382/130 |
| 6,370,417 B1 | * | 4/2002 | Horbaschek et al. | .......... 600/424 |
| 6,961,406 B2 | * | 11/2005 | Hayashi | ...................... 378/98.12 |
| 7,162,066 B2 | * | 1/2007 | Oosawa | .......................... 382/132 |
| 7,346,198 B2 | * | 3/2008 | Oosawa | .......................... 382/128 |
| 7,409,078 B2 | * | 8/2008 | Pescatore et al. | .............. 382/130 |
| 7,551,721 B2 | * | 6/2009 | Nakaura et al. | ............. 378/98.12 |
| 7,697,744 B2 | * | 4/2010 | Ohishi | ........................... 382/132 |
| 7,826,884 B2 | * | 11/2010 | Baumgart | ...................... 600/407 |
| 8,050,474 B2 | * | 11/2011 | Baumgart | ...................... 382/130 |

FOREIGN PATENT DOCUMENTS

| | | |
|---|---|---|
| JP | 1-100247 | 4/1989 |
| JP | 8-308822 | 11/1996 |
| JP | 2004-112469 | 4/2004 |

OTHER PUBLICATIONS

Office Action issued Aug. 9, 2011, in Japanese Patent Application No. 2006-042759 (with English-language translation).
Office Action issued Jun. 14, 2011, in Japanese Patent Application No. 2006-042759 (with English Translation).

* cited by examiner

*Primary Examiner* — Allen C. Ho
(74) *Attorney, Agent, or Firm* — Oblon, Spivak, McClelland, Maier & Neustadt, L.L.P.

(57) ABSTRACT

An image diagnostic apparatus includes a radiography unit which generates a mask image and contrast images before and after the injection of a contrast medium, an image memory which stores the mask image and the contrast images, an ROI identifying unit which sets a region of interest from the mask image and the contrast images, a pixel shift amount detecting unit which detects a pixel shift amount between the mask and the contrast image upon localization to the region of interest, and a processing unit which shifts at least the mask image or the contrast image in accordance with the detected pixel shift amount and performs subtraction between the images.

24 Claims, 10 Drawing Sheets

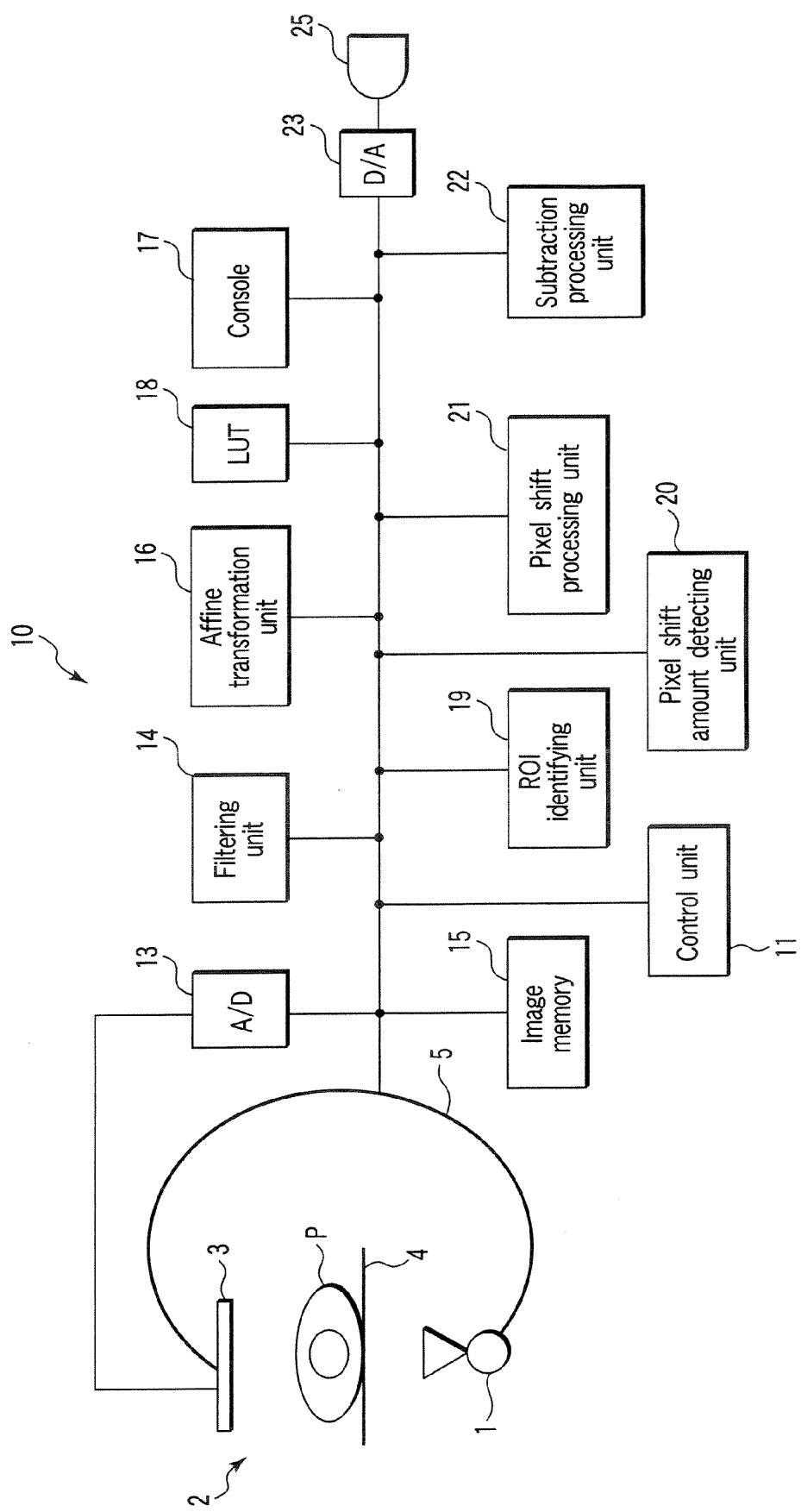
F I G. 1

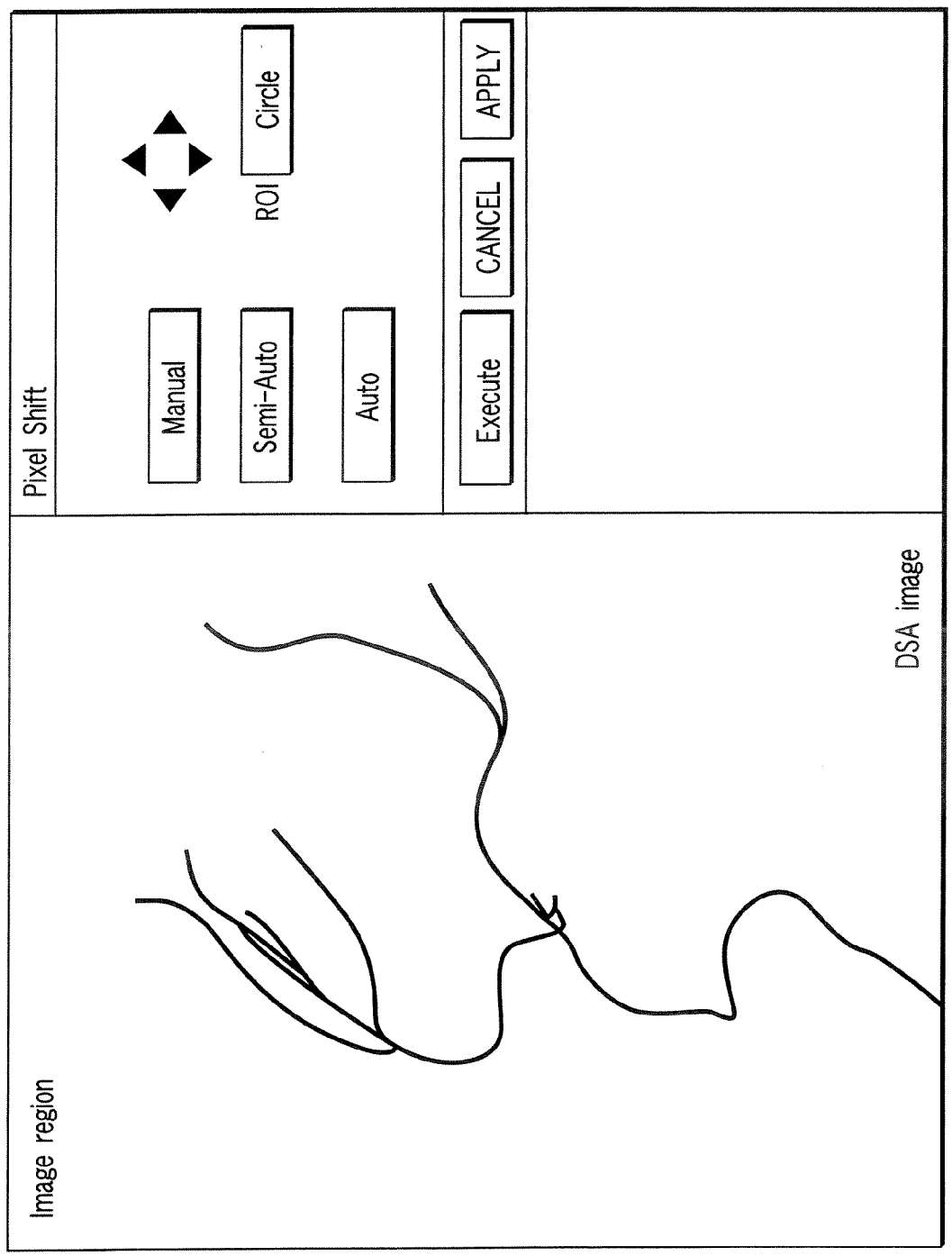
F I G. 2

IMAGE DIAGNOSTIC APPARATUS, IMAGE PROCESSING APPARATUS, AND PROGRAM

CROSS-REFERENCE TO RELATED APPLICATIONS

This application is based upon and claims the benefit of priority from prior Japanese Patent Application No. 2006-042759, filed Feb. 20, 2006, the entire contents of which are incorporated herein by reference.

BACKGROUND OF THE INVENTION

1. Field of the Invention

The present invention relates to an image diagnostic apparatus, image processing apparatus, and program which inject a contrast medium into a subject and perform subtraction processing between images before and after the injection of the contrast medium.

2. Description of the Related Art

In DSA examination of the head of a patient, abrupt injection of a contrast medium into the patient may cause lack of oxygen and causalgia. This causalgia causes the patient to move, and produces motion artifacts on subtraction images (also called DSA images). In this case, pixel shifting is manually performed, or semi-automatically performed upon designation of an ROI (Jpn. Pat. Appln. KOKAI Publication No. 2004-112469).

Motion artifacts appear variously and often change for each frame. In such a case, pixel shifting needs to be performed for each frame. In addition, some patients tend to cause motion artifacts, and hence correction is often performed in many series (images acquired as moving images by one injection of a contrast medium). Under the circumstances, it requires a great deal of labor to perform correction even in automatic pixel shifting.

BRIEF SUMMARY OF THE INVENTION

It is an object of the present invention to reduce the operation load on an operator in pixel shift processing for reducing motion artifacts mainly caused by the body movement of a subject when subtraction processing is performed between images before and after the injection of a contrast medium.

According to the present invention, there is provided an apparatus comprising a radiography unit which generates a mask image and a contrast image before and after injection of a contrast medium, an image storage unit which stores the mask image and the contrast image, a region setting unit which sets a region of interest from the mask image and the contrast image, a pixel shift amount detecting unit which detects a pixel shift amount between the mask image and the contrast image upon localization to the region of interest, and a processing unit which shifts at least one of the mask image and the contrast image in accordance with the detected pixel shift amount and performs subtraction between the images.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray diagnostic apparatus according to an embodiment of the present invention;

FIG. 2 is a view showing an example of an initial window for pixel shift processing in this embodiment;

DETAILED DESCRIPTION OF THE INVENTION

Figure 3:
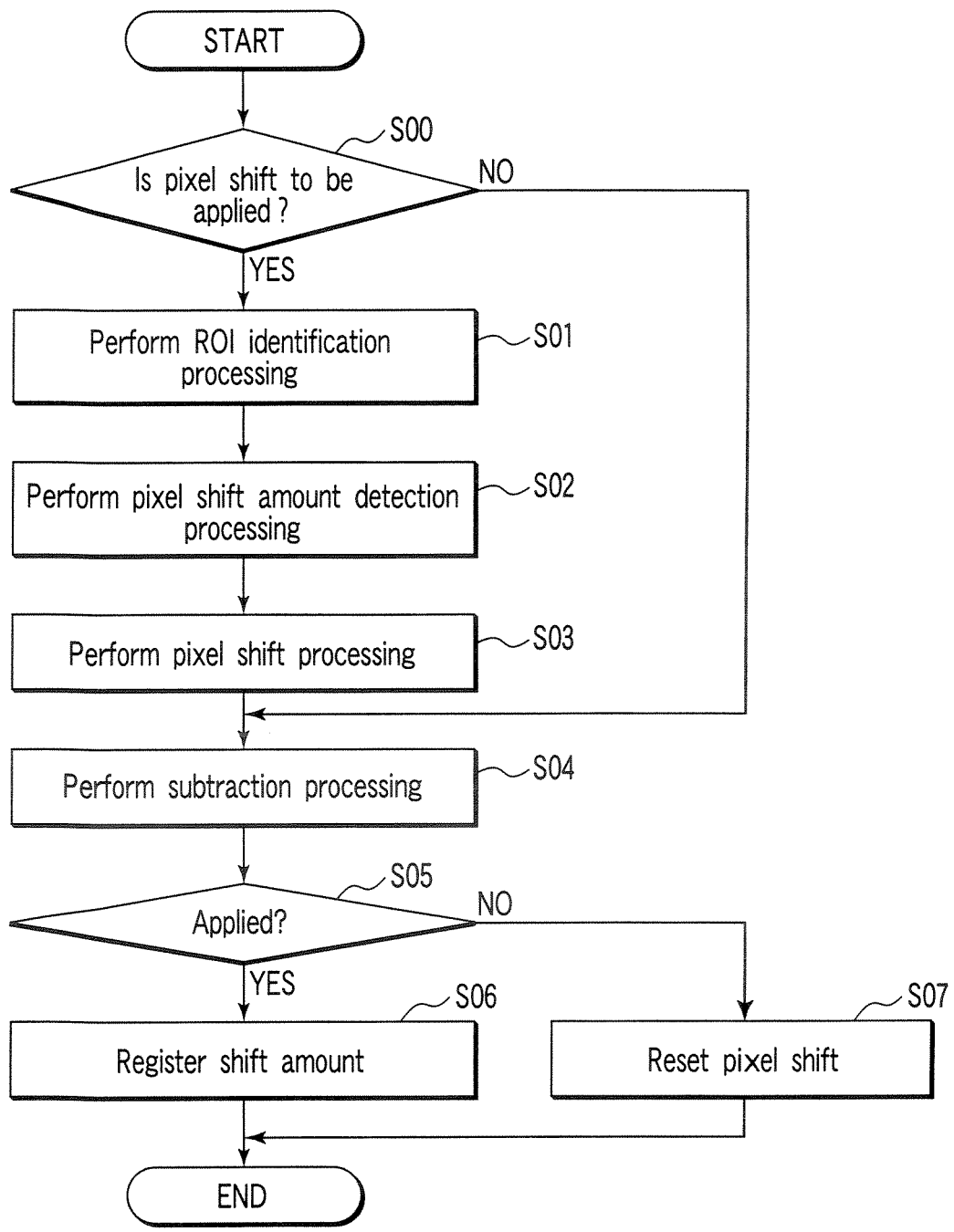
FIG. 3 is a flowchart showing a pixel shift processing procedure in this embodiment.

A preferred embodiment of the present invention will be described below with reference to the views of the accompanying drawing. Note that the present invention includes an image diagnostic apparatus which can acquire contrast images and non-contrast images. This type of image diagnostic apparatus includes an X-ray diagnostic apparatus, ultrasonic diagnostic apparatus, magnetic resonance imaging apparatus, PET, and SPECT. Any of these apparatuses can be applied to the present invention. The following will exemplify an X-ray diagnostic apparatus.

FIG. 1 shows the arrangement of an X-ray diagnostic apparatus according to this embodiment. A radiography unit (image acquisition unit) 2 includes an X-ray tube 1 and an X-ray detector 3 which face each other through a subject P placed on a bed top 4. A C-arm 5 holds the X-ray tube 1 and the X-ray detector 3. A support mechanism (not shown) supports the C-arm 5 so as to allow it make multiaxial rotation and movement. This apparatus uses a flat panel detector (FPD) including a scintillator and a photodiode array as the X-ray detector 3. However, the apparatus may use a combination of an image intensifier and a TV camera as the X-ray detector 3. An injector (not shown) for automatically injecting a contrast medium into the subject P is placed beside the bed top. An image processing apparatus 10 receives an analog video signal output from the X-ray detector 3 through an analog/digital converter (A/D) 13.

In addition to the analog/digital converter 13, the image processing apparatus 10 includes a control unit 11, a filtering processing unit 14 which performs filtering processing such as high-frequency enhancement filtering with respect to the X-ray image data which is generated by the radiography unit 2 and converted into a digital signal by the analog/digital converter 13, an image memory 15 which stores the X-ray image data before and after filtering processing, an affine transformation unit 16 which performs image enlargement/movement with respect to the X-ray image data, a console 17, a lookup table (LUT) 18 which performs grayscale conversion, an ROI identifying unit 19, a pixel shift amount detecting unit 20, a pixel shift processing unit 21, a subtraction processing unit 22, a digital/analog converter (D/A) 23, and a display 25.

Of a plurality of X-ray images repeatedly radiographed before and after the injection of a contrast medium, an X-ray image before the injection of the contrast medium, more accurately before the contrast medium flows into a radiographic region, is identified as a mask image, and X-ray images after the injection of the contrast medium, more accurately after the contrast medium flows into the radiographic region, are identified as contrast images. Since a contrast medium is injected into a blood vessel, a contrast image includes both a region (contrast region) mainly occupied by a blood vessel with density being increased by the contrast medium and a region (non-contrast region) where no density change has occurred. On the other hand, a mask image substantially includes no contrast region and is occupied by a non-contrast region.

The ROI identifying unit 19 identifies a processing target region (to be referred to as a region of interest ROI) for the processing (pixel shift amount detection processing) of identifying a moving amount (pixel shift amount) for eliminating the positional shift between a mask image before the injection of contrast medium and a contrast image after the injection of the contrast medium which is mainly caused by the body movement of a subject. The pixel shift amount detecting unit 20 detects the positional shift (pixel shift amount) between a contrast image after the injection of a contrast medium and a mask image before the injection of the contrast medium upon localization to the detected region of interest ROI. The subtraction processing unit 22 generates a subtraction image by shifting at least one of a mask image and a contrast image in accordance with a pixel shift amount and performing subtraction between the images. The display 25 directly receives the subtraction image through the digital/analog converter 23 and displays it.

Mask selecting operation by this embodiment will be described below.

In contrast medium radiography, this apparatus repeats radiography before and after the injection of a contrast medium. In practice, the contrast medium is injected almost at the same time when the apparatus starts radiography. When the image memory 15 stores X-ray image data, the apparatus generally handles the image of the first frame as a mask image and the images of the subsequent frames as contrast images. Typically, in DSA (digital subtraction angiography), the apparatus subtracts a mask image from a contrast image. The display 25 displays the subtraction image as an image with a contrast region, i.e., a contrast-enhanced blood vessel region, being left and enhanced. Injection of a contrast medium, more specifically, abrupt injection of a contrast medium for examination of the head of a subject, may cause lack of oxygen and causalgia. If this causalgia causes the patient to move, motion artifacts occur on a subtraction image (also called a DSA image). Upon determining the occurrence of motion artifacts, the observer executes pixel shifting for motion artifact correction. As shown in FIG. 2, the apparatus prepares three kinds of modes, i.e., the manual mode, semi-automatic mode, and automatic mode, for pixel shift processing under the control of the control unit 11 in accordance with how much the processing is to be manually performed.

In setting the manual mode, when the operator turns on the manual button written as [Manual] through the console 17, the button is set in a depressed state. In this state, the manual pixel shift processing function by the console 17 and the pixel shift processing unit 21 is validated. When the operator presses this button again, the button returns to the projected state, thereby invalidating the manual pixel shift processing function. While this mode is valid, when the operator shifts a mask image by operating the up, down, right, and left keys (↑, ↓, →, and ←) of the keyboard with a contrast image being fixed, the subtraction processing unit 22 subtracts the mask image shifted by the pixel shift processing unit 21 on the basis of the operation result and the contrast image to generate a subtraction image. The apparatus then displays this image on an image area on the display 25. The operator can perform the same operation by pressing the buttons located beside the manual button on the window. In addition, when the operator moves the mouse cursor to the image area and moves the mouse while pressing the right mouse button inside the image area to move a mask image in the corresponding direction, the apparatus can display a subtraction image on the basis of the operation result. When achieving an optimal shift amount, the operator presses the execution key written as [Execute] to confirm the shift amount. Operating this execution key will display a frame on the basis of the result of the application of the shift amount confirmed afterward. The operator further presses the application key to apply the shift amount to all subsequent frames. Operating this application key will display all frames after the currently display frame on the basis of the result of the application of the shift amount confirmed afterward.

In setting the semi-automatic mode, when the operator turns on the semi-automatic button written as [Semi-Auto], the button is set in the depressed state. In this state, the semi-automatic pixel shift processing function is validated. When the operator presses this button again, the button returns to the projected state, thereby invalidating the semi-automatic pixel shift processing function. When the semi-automatic pixel shift processing function is validated, the apparatus displays a mark indicating a region of interest ROI on a subtraction image first. The operator can select a rectangular shape, a circular shape, or the like for the region of interest ROI. When the operator selects a circular shape as an ROI mark, the apparatus displays the circular ROI mark on the subtraction image. The operator can move and enlarge/reduce this ROI mark by a user interface similar to that used for a general graphics drawing function. The operator sets the ROI mark so as to contain a region where an artifact has occurred, and presses the execution key to detect a pixel shift amount. When the operator presses the execution key, the apparatus computes correlations while the operator gradually shifts the mask image up, down, left, and right within the region of interest ROI. Identifying the moving amount by which the highest correlation is obtained as an optimal shift amount makes it possible to display the subtraction image on the basis of the shift amount. In order to apply the shift amount to all subsequent frames, the operator presses the application key. Operating this application key will display all subsequent frame after the currently displayed frame on the basis of the result of the application of the shift amount confirmed afterward.

In setting the automatic mode, when the operator turns on the automatic button, the button is set in the depressed state, and the apparatus starts processing. When the processing is complete, the button returns to the initial state. FIG. 3 shows a specific flowchart for the processing. The following is a case wherein the apparatus acquires X-ray images of (M+1) frames, and displays M subtraction images by setting one of the frames as a mask image and the M frames as contrast images. In this case, the mask image is a frame set by default. In general, the first frame acquired first after the start of radiography is set as a mask image.

Under the control of the control unit 11, the subtraction processing unit 22 subtracts a mask image from each of contrast images sequentially read out from the image memory 15 in accordance with the radiography order to sequentially generate subtraction images, and the display 25 consecutively displays the subtraction images. Upon determining that many motion artifacts have occurred on a displayed subtraction image, the observer presses the automatic button through the console 17 when the subtraction image is displayed. Assume that this frame is the kth frame of the subtraction images. When the operator presses the automatic button, the ROI identifying unit 19 identifies the region of interest ROI. Subsequently, the pixel shift amount detecting unit 20 identifies a pixel shift amount by processing localized to the region of interest ROI. Furthermore, the pixel shift processing unit 21 pixel-shifts the mask image in accordance with the detected pixel shift amount. Finally, the subtraction processing unit 22 generates a subtraction image by subtraction between a contrast image and the pixel-shifted mask image. The following will describe the contents of each step in detail.

In step S00, the control unit 11 determines, in accordance with an instruction input by the operator through the console 17, whether to apply pixel shift processing. When determining to apply pixel shift processing, the control unit 11 performs the following processing.

In ROI identification step S01, the ROI identifying unit 19 obtains an artifact intensity Ep(i, j) by using a subtraction image as follows:

$$E_p(i,j) = f[Sk(i,j)] \quad (1)$$

where Sk(i, j) is the subtraction image of the kth frame, and f(x) is defined as follows:

$$f(x) = \begin{cases} x: x \geq 0 \\ 0: x < 0 \end{cases} \quad (2)$$

Upon determining on the basis of the above result that Ep(i, j)>E, the control unit 11 registers the corresponding pixel as a target region. In this case, E is a predetermined threshold.

That is, the ROI identifying unit 19 calculates, as the artifact intensity Ep(i, j), the total sum of the pixel values of pixels appearing with reverse polarity (typically, positive polarity including zero) with respect to a contrast medium (negative polarity) throughout the M subtraction images. The ROI identifying unit 19 determines a pixel group whose artifact intensity Ep(i, j) exceeds the threshold E as the initial (primary) region of interest ROI. Most of pixels appearing with reverse polarity to pixels based on the contrast medium after subtraction processing are generated due to the body movement of the subject. The body movement generates pixels with the same polarity as that of the contrast medium and pixels with reverse polarity to the contrast medium. Discriminating whether a pixel appearing with the same polarity as that of a pixel based on the contrast medium is generated by the contrast medium or body movement tends to cause an error. However, most of pixels appearing with reverse polarity to pixels based on the contrast medium after subtraction processing are generated by body movement. Therefore, setting a pixel appearing with reverse polarity to a pixel based on the contrast medium will ensure high accuracy in specifying a region influenced by body movement.

The control unit 11 removes a region located outside a predetermined range from the primarily determined region of interest ROI, thereby generating a secondary region of interest ROI. This is because a region of interest in a clinical point of view is generally located near the center of an image, and the occurrence of a motion artifact in the region poses the most serious problem.

Figure 4A:
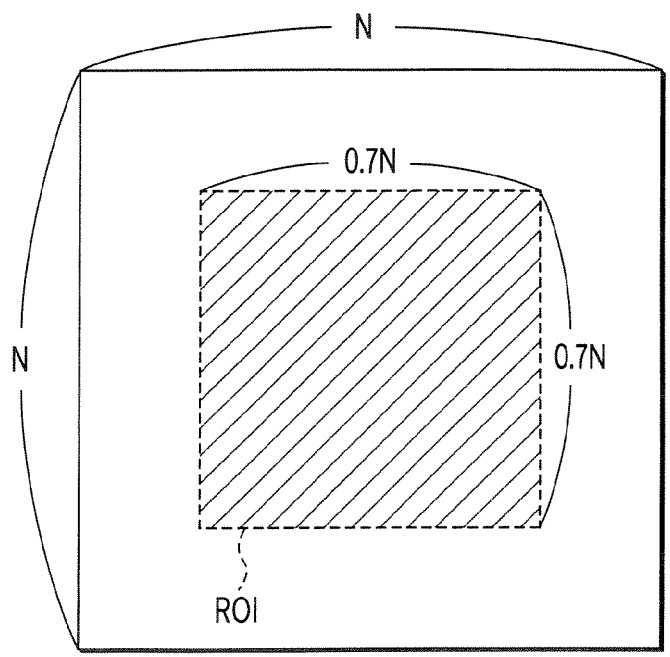
FIG. 4A is a view showing an example of an ROI detected in ROI identification processing step SO1 in FIG. 3.

Assume that a 0.7N×0.7N region in the center of an entire image (N×N) is set as a target region, as shown in FIG. 4A. A region where the target region overlaps the primary region of interest ROI is set as the secondary region of interest ROI. In other words, the secondary region of interest ROI is determined by removing an annular region other than the central 0.7N×0.7N region from the primary region of interest ROI.

The control unit 11 determines a final region of interest ROI by expanding the secondary region of interest ROI up, down, left, and right to a predetermined range (expansion processing). The final region of interest ROI will be simply referred to as the region of interest ROI. The control unit 11 performs expansion processing because it is highly probable that there is information associated with an artifact near a region where the artifact has occurred (for example, there is an artifact with negative polarity (based on the contrast medium) near an artifact region with positive polarity (not based on the contrast medium), or an artifact is underevaluated by a threshold process). Consider an arbitrary pixel. In this case, if there is an artifact region within a radius of 10 pixels, the arbitrary pixel is regarded as an artifact region.

Figure 4B:
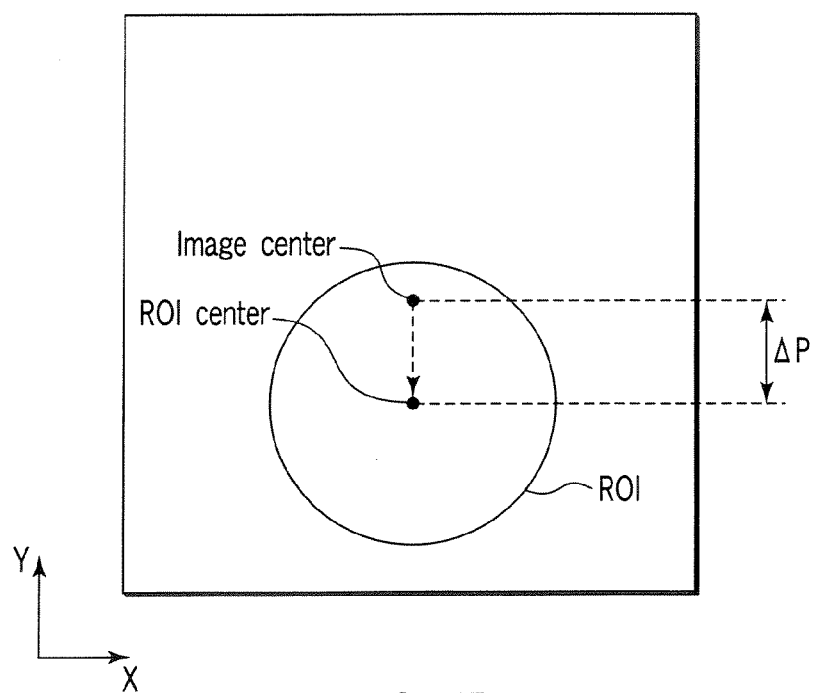
FIG. 4B is a view showing an example of an ROI automatically set with respect to the skull base in ROI identification processing step S01 in FIG. 3.

In addition, in a case of a head image, as shown in FIG. 4B, it is effective to set a region including at least part of the skull base as a secondary or final region of interest ROI. This is because a skull base portion has a complicated bone structure, and many residual pixels are generated on a subtraction image due to the influence of a motion artifact. In practice, the control unit 11 sets, as the center of the region of interest ROI, a position separated from the image center by a predetermined distance ΔP (a predetermined number of pixels) in the direction from the vertex to the jaw, typically in the negative Y-axis direction.

In pixel shift amount detection processing step S02, the pixel shift amount detecting unit 20 repeatedly computes correlations between the mask image and the contrast images by finely moving the mask image within a search region in a predetermined range from the same position on the mask image upon localizing to the detected region of interest ROI. The pixel shift amount detecting unit 20 determines the position where the lowest computation result (correlation coefficient) is obtained as a corresponding position, and stores a moving vector to the position as pixel shift amount data. In this case, correlation computation can be written as $$CR(\Delta i, \Delta j) = \sum_{i=1}^{N} \sum_{j=1}^{N} [r\{C_k(i, j) - M(i+\Delta i, j+\Delta j)\}]^2 \quad (3)$$

where Ck(i, j) and M(i+Δi, j+Δj) are respectively the contrast image and mask image of the kth frame, N is the matrix size of the image, (Δi, Δj) is a shift vector, and CR(Δi, Δj) is a correlation computation result. The pixel shift amount detecting unit 20 obtains correlation computation results while shifting Δi and Δj between −Δ and Δ, and detects, as a positional shift, a shift vector by which the correlation computation result is minimized. The range of correlation computation is defined by $-\Delta$ and $\Delta$, and a step in computation (step of $\Delta i$ and $\Delta j$) is represented by $\delta$. In addition, r(x) is defined as follows:

$$r(x) = \begin{cases} x0: \text{within ROI} \\ o: \text{outside ROI} \end{cases} \quad (4)$$

The following description is based on the assumption that ($\Delta i0$, $\Delta j0$) is a shift vector by which CR($\Delta i$, $\Delta j$) is minimized. In pixel shifting step S03, the pixel shift processing unit 21 shifts the mask image by the vector ($\Delta i0$, $\Delta j0$). In subtraction step S04, the control unit 11 subtracts a contrast image Ck(i, j) and a shifted mask image M(i+$\Delta i0$, j+$\Delta j0$). The control unit 11 sequentially displays subtraction images.

When the observer approves the result and presses the execution button, the control unit 11 registers ($\Delta i0$, $\Delta j0$) as an optimal pixel shift amount for the kth frame in a region attached to the subtraction image. When displaying the same image next, the control unit 11 uses the result obtained by the registered pixel shift amount and displaying it. When the observer does not approve the result and presses the cancellation button, the control unit 11 deletes the result (S07). When the observer is to apply the same pixel shift amount to the succeeding frame upon approval of the result (S06), he/she presses the application button in step S05.
(First Modification)

Figure 5:
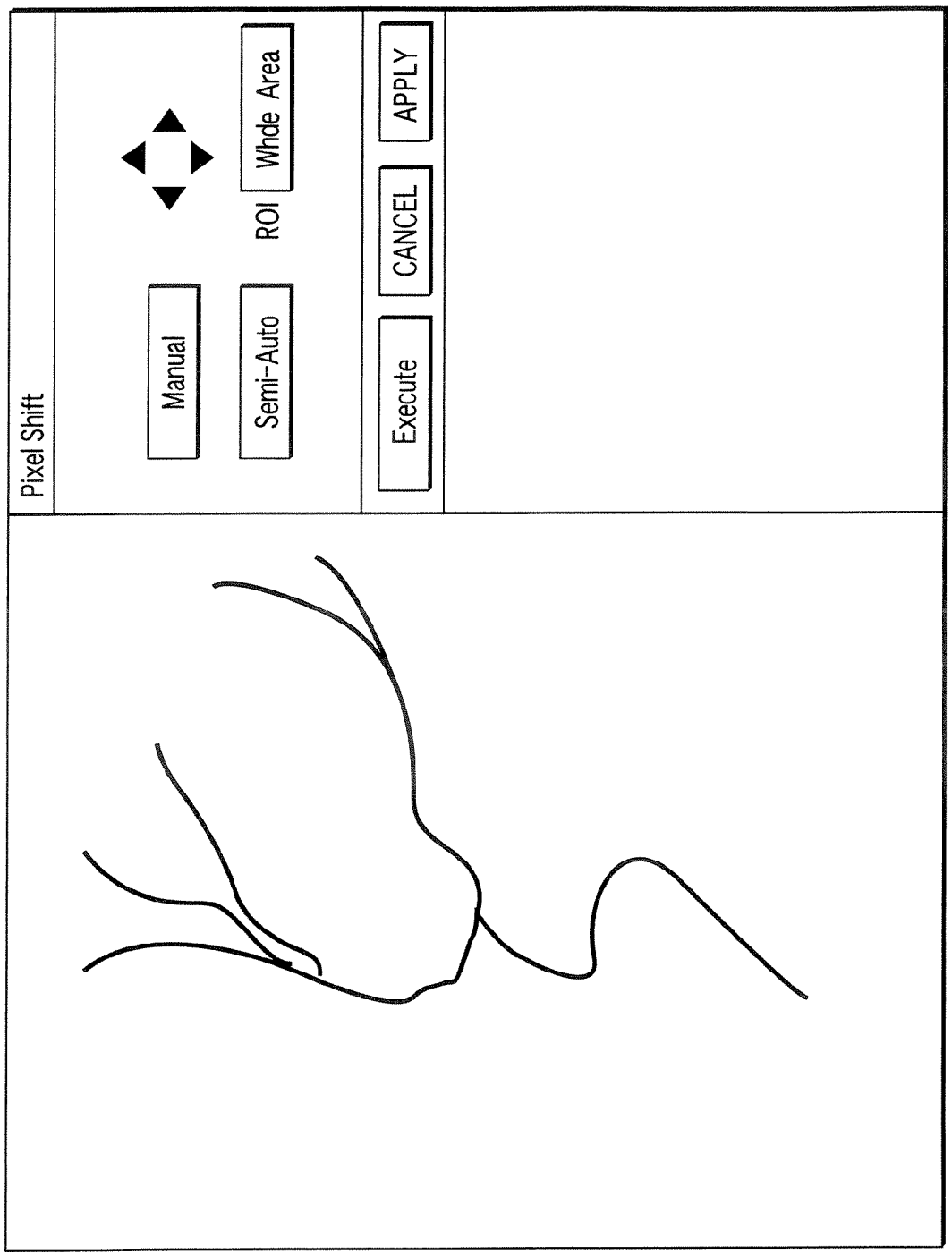
FIG. 5 is a view showing another example of the initial window for pixel shift processing in this embodiment.

According to the above description, the above embodiment includes the automatic button. Even if, however, a region of interest ROI is set as an entire image with a semi-automatic button, it suffices to apply the algorithm for automatically setting a region of interest ROI, as shown in FIG. 5.
(Second Modification)

Figure 6:
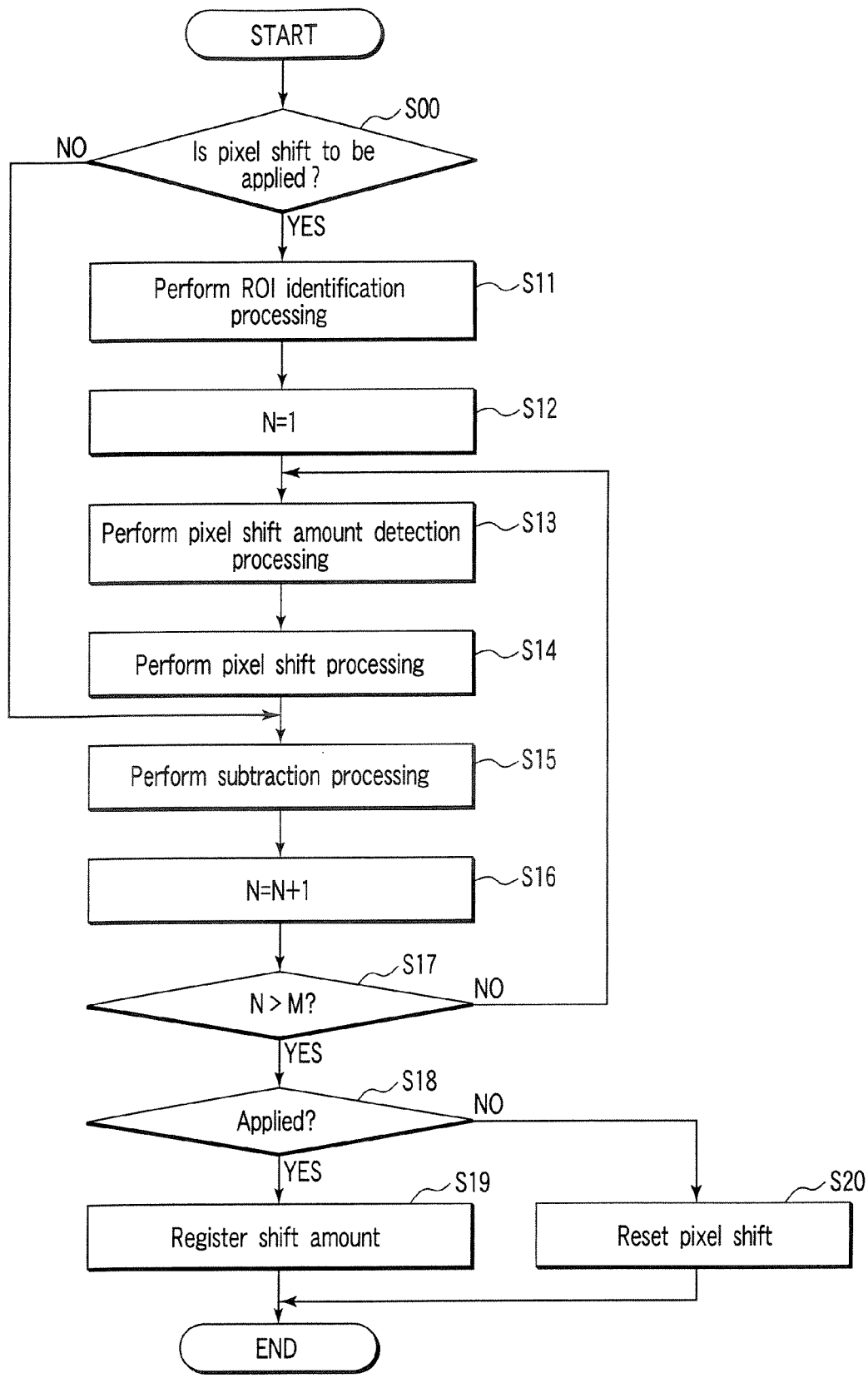
FIG. 6 is a view showing a modification of the pixel shift processing procedure in FIG. 3.

FIG. 6 shows a flowchart for a processing procedure based on a second modification. According to the above description, a region of interest is optimized with respect to only a display frame. However, it suffices to set an optimal region of interest ROI common to all the M contrast images.

As in the above case, in setting the automatic mode, when the operator turns on the automatic button, the button is set in depressed state, and the apparatus starts processing. When the processing is complete, the button returns to the initial state. The following will describe a case wherein the apparatus acquire (M+1) images, and displays M subtraction images by setting one of the frames as a mask image and the M frames as contrast images. In this case, the mask image is a frame set by default. In general, the first frame is set as a mask image. First of all, a region of interest ROI is identified by using the M subtraction images. Thereafter, the apparatus detects a pixel shift amount for each contrast image, pixel-shifts the mask image on the basis of the detected shift amount, and executes subtraction between the contrast image and the corrected mask image. The apparatus performs this operation for each of the contrast images of all the M frames. The contents of each step will be described in detail next.

In ROI identification step S11, the control unit 11 obtains the artifact intensity Ep(i, j) and an artifact frequency Fp(i, j) by using the M generated subtraction images in the following manner.

$$E_p(i, j) = \sum_{k=1}^{M} f[S_k(i, j)] \quad (5)$$

$$F_p(i, j) = \sum_{k=1}^{M} g[S_k(i, j) - S] \quad (6)$$

where Sk(i, j) is the subtraction image of the kth frame, and S is a predetermined constant which discriminates an artifact from noise in Sk(i, j). Then f(x) and g(x) are defined as follows:

$$f(x) = \begin{cases} x: x \geq 0 \\ 0: x < 0 \end{cases} \quad (7)$$

$$g(x) = \begin{cases} 1: x \geq 0 \\ 0: x < 0 \end{cases} \quad (8)$$

As described above, the control unit 11 obtains the artifact intensity Ep(i, j) by calculating total sum of the pixel values of pixels appearing with reverse polarity (typically, positive polarity including zero) to a contrast medium (negative polarity) throughout the M subtraction images.

On the other hand, the control unit 11 obtains the artifact frequency Fp(i, j) by obtaining the frequency (the number of pixels) at which the pixel value of a pixel appearing with positive polarity exceeds a predetermined threshold for each pixel with respect to the M subtraction images between the mask image and the M contrast images.

The control unit 11 determines, as the region of interest ROI, a pixel group which satisfies Ep(i, j)>E and Fp(i, j)>F on the basis of the above result. In this case, E and F are predetermined thresholds. The following is an example of a combination of a means for calculating the total sum of positive pixel values and a means for calculating the number of pixels (frequency) each which exceeds a threshold. The means for calculating the frequency of pixels each of which exceeds a threshold may be combined with a means for calculating the maximum absolute value of a positive or negative signals for each pixel instead of the means for calculating the total sum of positive signals. Furthermore, it suffices to singly use one of the three means.

A region outside a predetermined range inside the region of interest ROI is deleted from a registered region. This is because a target region in a clinical point of view is generally located near the center of an image, and the occurrence of a motion artifact in the region poses the most serious problem. In this case, as shown in FIG. 4A, a region other than the 0.7N×0.7N region of the entire image is set as a region outside a target region, and an artifact region outside the range is deleted from the region.

The control unit 11 further expands the registered region of interest ROI up, down, left, and right to a predetermined range. This is because it is highly probable that there is information associated with an artifact near a region where the artifact has occurred (for example, there is an artifact with negative polarity near an artifact region with positive polarity, or an artifact is underevaluated by a threshold process). Consider an arbitrary pixel. In this case, if there is an artifact region within a radius of 10 pixels, the arbitrary pixel is regarded as an artifact region.

The control unit 11 repeats the processing from pixel shift amount detection step S13 to subtraction processing step S15 for each contrast image through variable N initialization step S12, variable N increment step S16, and step S17 of determining whether the variable N has reached a contrast image count M. In pixel shift amount detection step S13, the control unit 11 sequentially performs correlation computation while finely moving the mask image within a search region in a predetermined range from the same position on an image. The control unit 11 then determines a position where the lowest computation result is obtained as a corresponding position, and stores a moving vector to the position. In this case, correlation computation can be written as $$CR(\Delta i, \Delta j) = \sum_{i=1}^{N} \sum_{j=1}^{N} [r\{C_k(i, j) - M(i + \Delta i, j + \Delta j)\}]^2 \quad (9)$$

where $C_k(i, j)$ and $M(i+\Delta i, j+\Delta j)$ are respectively the contrast image of the kth frame and mask image of the kth frame, N is the matrix size of the image, $(\Delta i, \Delta j)$ is a shift vector, and $CR(\Delta i, \Delta j)$ is a correlation computation result. The control unit 11 obtains correlation computation results while shifting $\Delta i$ and $\Delta j$ between $-\Delta$ and $\Delta$, and detects, as a positional shift, a shift vector by which the correlation computation result is minimized. The range of correlation computation is defined by $-\Delta$ and $\Delta$, and a step in computation (step of $\Delta i$ and $\Delta j$) is represented by $\delta$. In addition, $r(x)$ is defined as follows:

$$r(x) = \begin{cases} x0: \text{ within } ROI \\ o: \text{ outside } ROI \end{cases} \quad (10)$$

The following description is based on the assumption that $(\Delta i0, \Delta j0)$ is a shift vector by which $CR(\Delta i, \Delta j)$ is minimized. In the pixel shifting step, the control unit 11 shifts the mask image by the vector $(\Delta ik, \Delta jk)$. In the subtraction step, the control unit 11 performs subtraction between $C_k(i, j)$ and a corrected mask image $M(i+\Delta ik, j+\Delta jk)$. The control unit 11 sequentially displays subtraction results.

When the observer approves the result and presses the execution button (S18), the control unit 11 registers an optimal shift $(\Delta ik, \Delta jk)$ for each frame in a region attached to the subtraction image (S19). The automatic button then returns to the initial state. When displaying the same image next, the control unit 11 uses the result obtained by the registered pixel shift amount and displays it. When the observer does not approve the result and presses the cancellation button, the result is reset (S20).

(Third Modification)

According to the above description, it is a fundamental principle that a region of interest ROI is identified from an artifact occurrence region. However, it suffices to identify a region of interest ROI on the basis of a contrast-medium-injected region. In the ROI identification step, the control unit 11 obtains a contrast medium injection signal intensity Em(i, j) and a contrast medium injection signal frequency Fm(i, j) by using M generated subtraction images as follows:

$$E_m(i, j) = \sum_{k=1}^{M} INVf[S_k(i, j)] \quad (11)$$

$$F_m(i, j) = \sum_{k=1}^{M} INVg[S_k(i, j) + S] \quad (12)$$

where $S_k(i, j)$ is the subtraction image of the kth frame, and S is a predetermined constant which discriminates a contrast medium injection signal from noise in $S_k(i, j)$. Then, INVf(x) and INVg(x) are defined as follows:

$$INVf(x) = \begin{cases} 0: x \geq 0 \\ x: x < 0 \end{cases} \quad (13)$$

$$INVg(x) = \begin{cases} 0: x \geq 0 \\ 1: x < 0 \end{cases} \quad (14)$$

Upon determining on the basis of the above result that Em(i, j)<G and Fm(i, j)>H, the control unit 11 registers the corresponding pixel as a contrast-medium-injected region. In this case, G and H are predetermined thresholds. A contrast medium injected regions are excepted from the 0.7N×0.7N region centered in the entire image. The remained region is registered as a region of interest ROI. Note that this embodiment has exemplified the combination of the means for calculating the total sum of negative signals and the means for calculating the frequency of pixels each which exceeds a threshold. The means for calculating the frequency of pixels each of which exceeds a threshold may be combined with a means for calculating the minimum value projection of a negative signal for each pixel instead of the means for calculating the total sum of negative signals. Furthermore, it suffices to singly use one of the three means.

(Fourth Modification)

According to the above description, a region of interest ROI is identified from one of an artifact occurrence region and a contrast-medium-injected region. However, a region of interest ROI may be identified from a combination of them. More specifically, a contrast-medium-injected region is excluded from an artifact occurrence region.

(Fifth Modification)

According to the above description, the control unit 11 calculates a pixel shift amount. Calculating an optimal pixel shift amount for each frame makes it possible to perform correction with very high accuracy. This technique, however, greatly increase the calculation amount and may not be useful for a clinic case requiring high speed. The control unit 11 therefore calculates an optimal pixel shift for each frame group including a plurality of frames as a unit instead of calculating an optimal pixel shift amount for each frame.

The control unit 11 obtains an artifact signal intensity for each frame as follows:

$$E_p(k) = \sum_{i=1}^{N} \sum_{j=1}^{N} f[S_k(i, j)] \quad (15)$$

$$F_p(k) = \sum_{i=1}^{N} \sum_{j=1}^{N} g[S_k(i, j) - S] \quad (16)$$

$S_k(i, j)$ is the subtraction image of the kth frame, and S is a predetermined constant which discriminates an artifact from noise in $S_k(i, j)$. Then, f(x) and g(x) are defined as follows:

$$f(x) = \begin{cases} x: x \geq 0 \\ 0: x < 0 \end{cases} \quad (17)$$

-continued $$g(x) = \begin{cases} 1: x \geq 0 \\ 0: x < 0 \end{cases} \quad (18)$$

Figure 7:
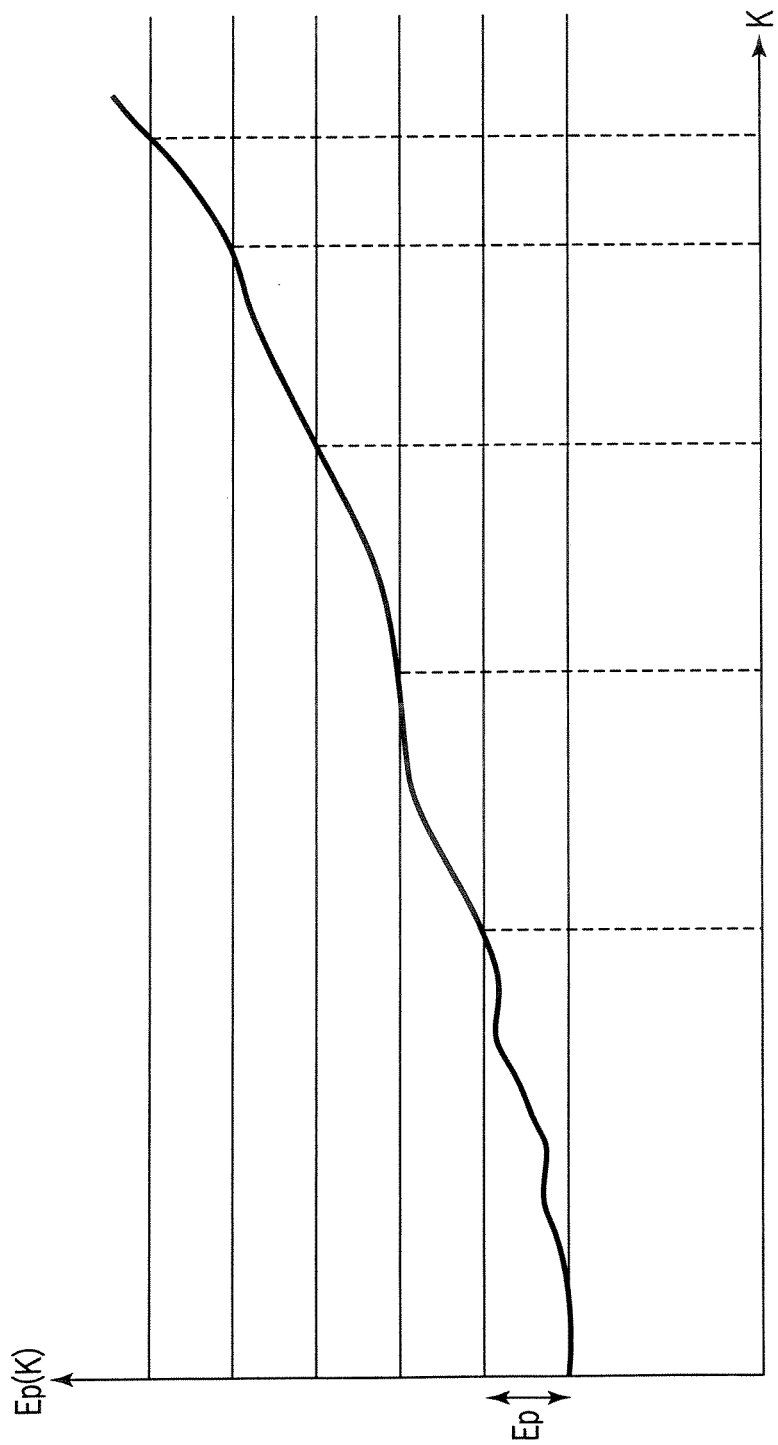
FIG. 7 is a graph showing the profile of artifact signal intensity in this embodiment.
Figure 8:
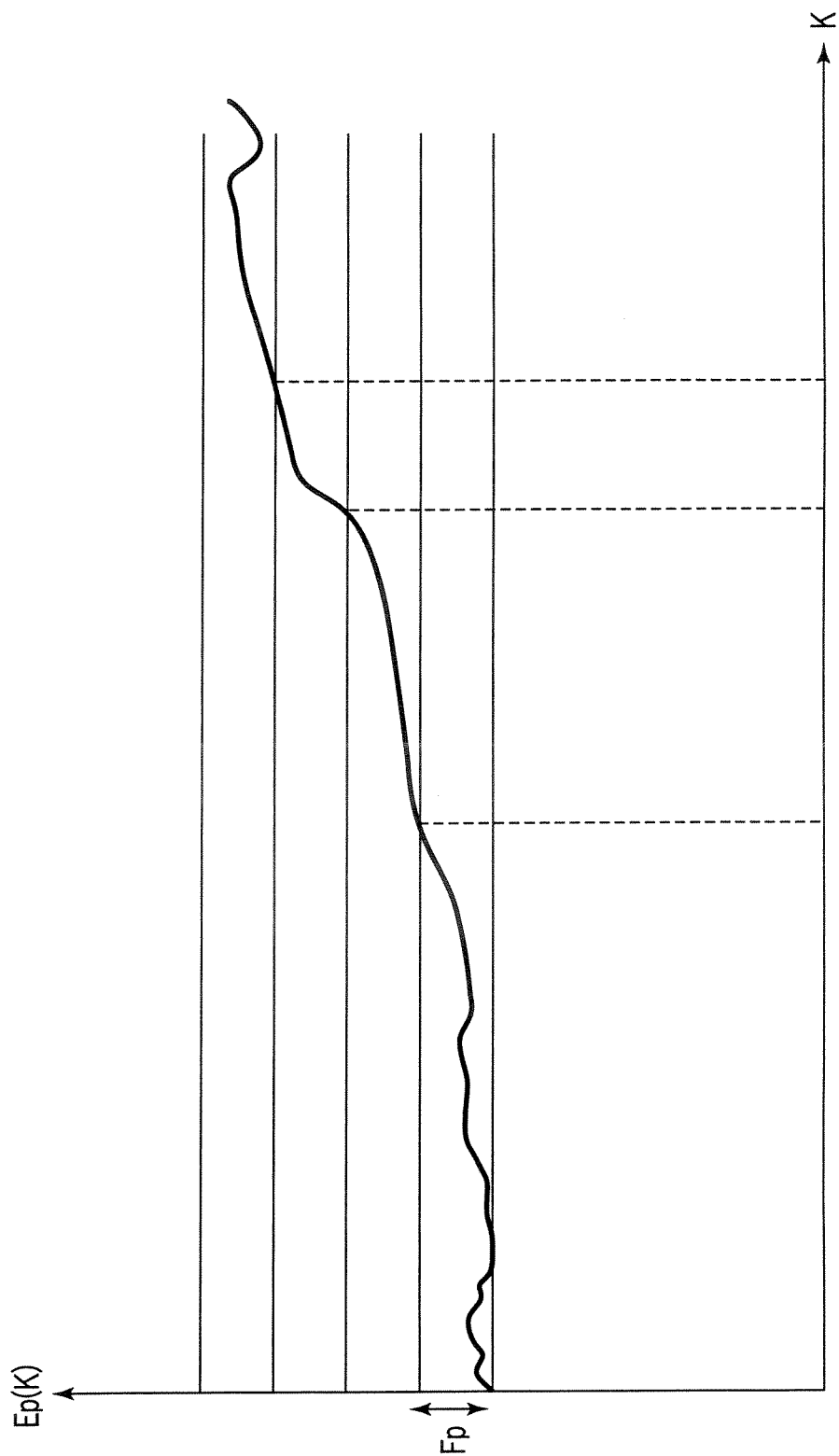
FIG. 8 is a graph showing the profile of an artifact occurrence frequency in this embodiment.

FIGS. 7 and 8 show the profiles of an artifact signal intensity and artifact occurrence frequency. Letting Ep and Fp be intervals at which frame groups are sorted, frames up to an earlier one of the first frame at which the error with respect to Ep(1) exceeds Ep and the first frame at which the error with respect to Fp(1) exceeds Fp are determined as a frame group. If the sth frame is a frame at which the above error exceeds Ep or Fp, frames up to an earlier one of the first frame at which the error with respect to Ep(s) exceeds Ep and the first frame at which the error with respect to Fp(s) exceeds Fp are determined as the next frame group. In this case, the control unit 11 determines a frame group by using both an artifact signal intensity and an artifact occurrence frequency. However, it suffices to determine a frame group by using one of them.

With the above processing, the control unit 11 determines frames ranging from the first frame to the (s−1)th frame as a single frame group. Assume that of the artifact signal intensity E and the artifact occurrence frequency F, the artifact signal intensity exceeds the threshold first. In this case, letting r be a frame nearest to the average or median of Ep(1) and Ep(s−1), the control unit 11 applies an optimal pixel shift amount (Δir, Δir) for the rth frame to the mask image, and subtracts it from the contrast images ranging from the first frame to the (s−1)th frame. In this case, the average functions to reduce errors in all the frames. In general, however, an artifact often changes abruptly, using the median may reduce artifacts more in terms of the overall moving image.

Assume that frames ranging from the sth frame to the (t−1)th frame are determined as a frame group, and the artifact occurrence frequency of the artifact signal intensity and the artifact occurrence frequency has exceeded the threshold first. If the uth frame is nearest to, for example, the median of Fp(s) and Fp(t−1), the control unit 11 applies an optimal pixel shift amount (Δiu, Δju) at the uth frame to the mask image and subtracts the mask image from the contrast images of the sth frame to the (t−1)th frame.

(Sixth Modification)

According to the above description, frame groups are sorted by using the artifact signal intensity E and the artifact occurrence frequency F. This method has a merit of a small calculation amount. Assume that after a shift has occurred to, for example, the right, an abrupt shift has occurred in the opposite direction by an amount twice that of the preceding shift. In this case, although the occurrence position of the artifact has actually changed, it can be regarded that no change has occurred in terms of the total amount of artifacts. In order to solve this problem, it is preferable to also perform calculation on the basis of the distribution of artifacts.

$$D_p(k) = \sum_{i=1}^{N} \sum_{j=1}^{N} \{f[S_k(i,j)] - f[S_s(i,j)]\}^2 \quad (19)$$

(N = 2 to M)

$$f(x) = \begin{cases} x: x \geq 0 \\ 0: x < 0 \end{cases} \quad (20)$$

where Dp is the difference value between artifact distributions of two images, and represents the total sum of positive and zero absolute values excluding negative values. Letting Dp be intervals at which frame groups are sorted, frames up to the first frames(s) at which the error with respect to Dp(1) exceeds Dp are determined as a frame group. With the above processing, frames ranging from the first frame to the (s−1)th frame are determined as a frame group. If the vth frame is nearest to the median of Dp(1) and Dp(s−1), the control unit 11 applies an optimal pixel shift amount (Δiv, Δjv) at the vth frame to the mask image, and subtracts the mask image from the contrast images of the first frame to the (s−1)th frame.

(Seventh Modification)

According to the above description, a pixel shift amount at an average frame of a frame group is set as a typical pixel shift amount. Postprocessing can be expected to obtain an effect of smoothing artifacts. From the viewpoint of real time performance (immediacy), this technique cannot determine a pixel shift amount up to, for example, the sth frame in the first frame group, and hence is very poor in real time performance. For this reason, when high real time performance is required, it is preferable to handle a pixel shift amount at the first frame in a frame group as a typical pixel shift amount.

(Eighth Modification)

According to the above description, a frame group is uniquely determined. This technique, however, needs to permit artifacts to some extent. On the other hand, processing for each frame instead of each frame group requires much calculation time. As a compromise between these techniques, the present invention may use a technique of performing processing for a frame group first, and then dividing the frame group upon completion of the processing.

More specifically, after the processing of the first frame group is complete, the control unit 11 divides the frame group of the frame groups at the first stage into two parts. Since the first frame group ranges from the first frame to the (s−1)th frame, the control unit 11 divides the frame group into a frame group ranging from the first frame to the {(s−1)/2}th frame and a frame group ranging from the {(s−1)/2+1}th frame to the (s−1)th frame, and recalculates optimal pixel shift amounts for the respective frame groups. The control unit 11 pixel-shifts the mask image on the basis of the recalculated pixel shift amount and executes subtraction, thereby sequentially reflecting the results in display in the order of completion. The control unit 11 processes the second frame group in the same manner as described above. Upon completing the processing of all the frame groups at the second stage, the control unit 11 further divides the second frame group. The control unit 11 then processes the third frame group in the same manner as described above. The control unit 11 continues this processing up to the frame unit. Note that the control unit 11 may terminate the processing when at least one of a minimum artifact intensity Epmin, a minimum artifact frequency Fpmin, and Dpmin or a combination thereof is satisfied.

(Ninth Modification)

Figure 9:
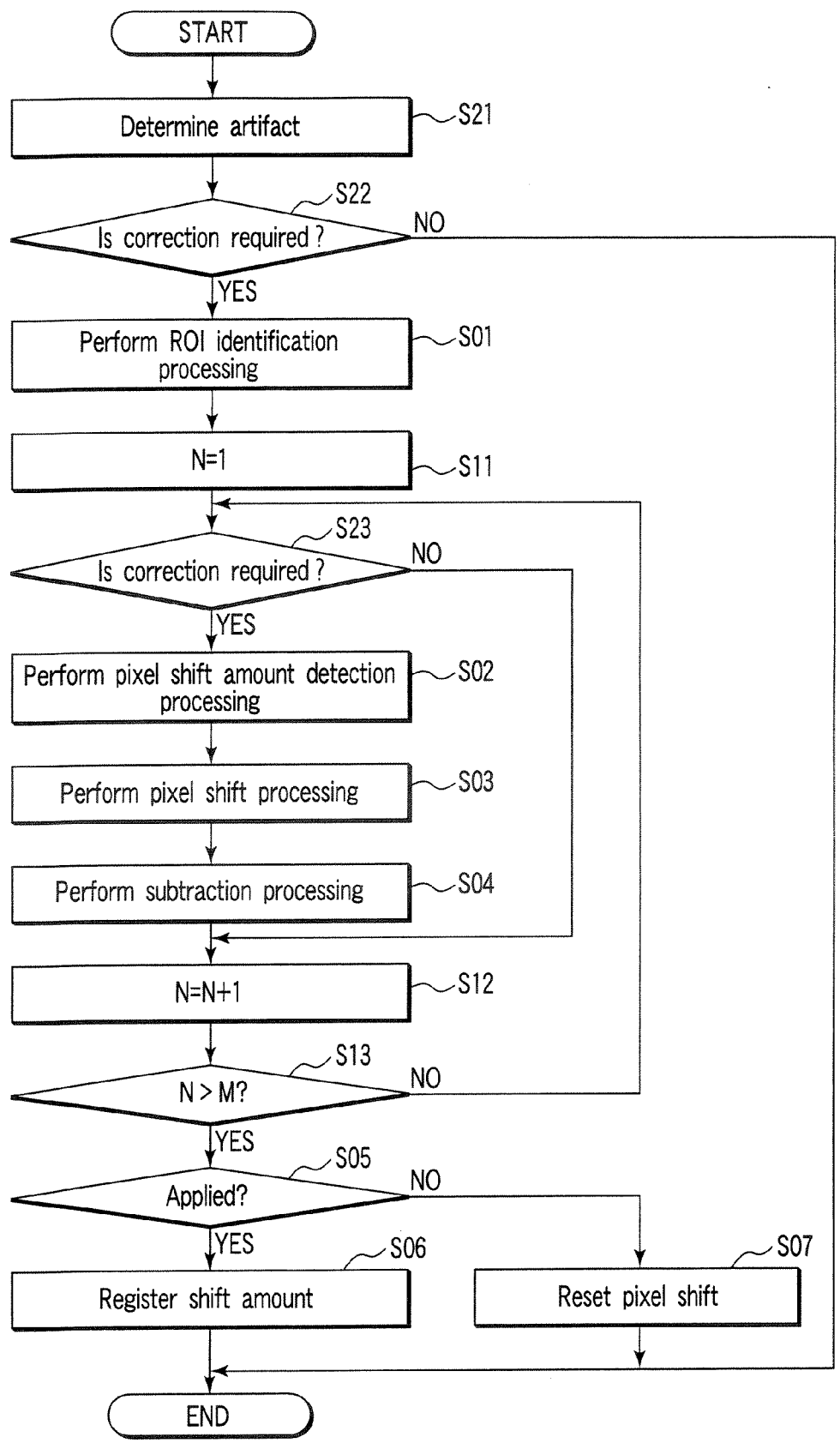
FIG. 9 is a flowchart showing another modification of the pixel shift processing procedure in FIG. 3.

A description of the same part as that described above will be omitted. FIG. 9 shows an operation procedure in this modification. According to the above embodiment, the observer determines the start of pixel shifting. In this modification, the start of this operation is automatically determined with respect to a radiographed image This modification includes a switch for determining during the execution of a radiography program whether to automatically perform pixel shifting. If this switch is turned on, the following processing is performed. If the switch is turned off, normal processing is performed.

Figure 10A:
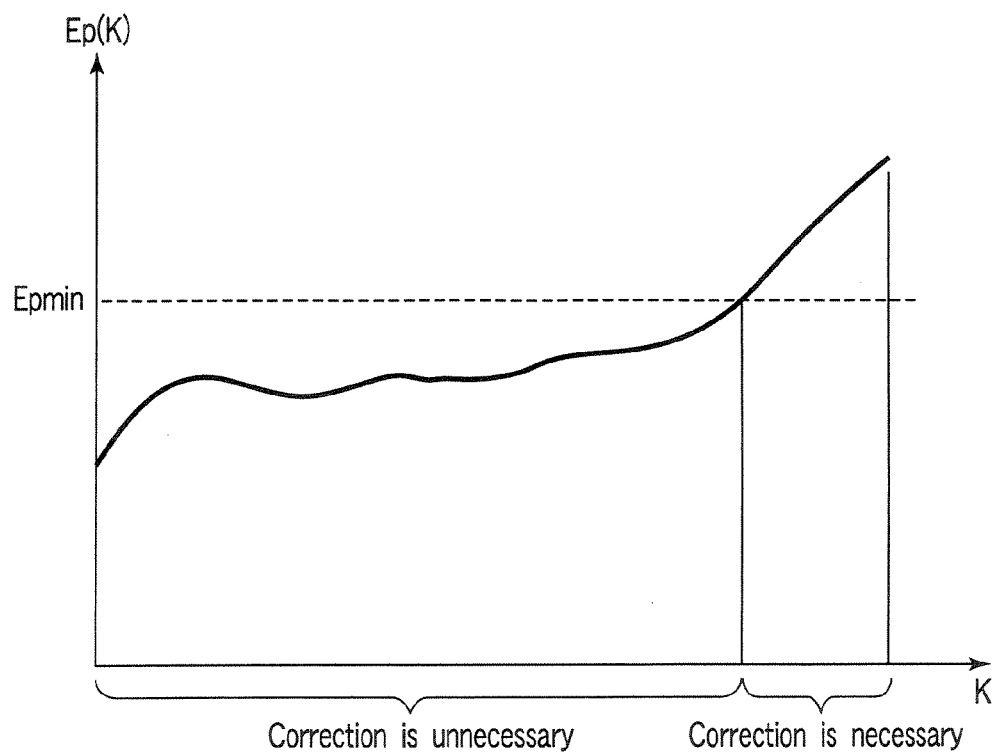
FIG. 10A is a graph showing an artifact intensity profile Ep(k) in this embodiment.
Figure 10B:
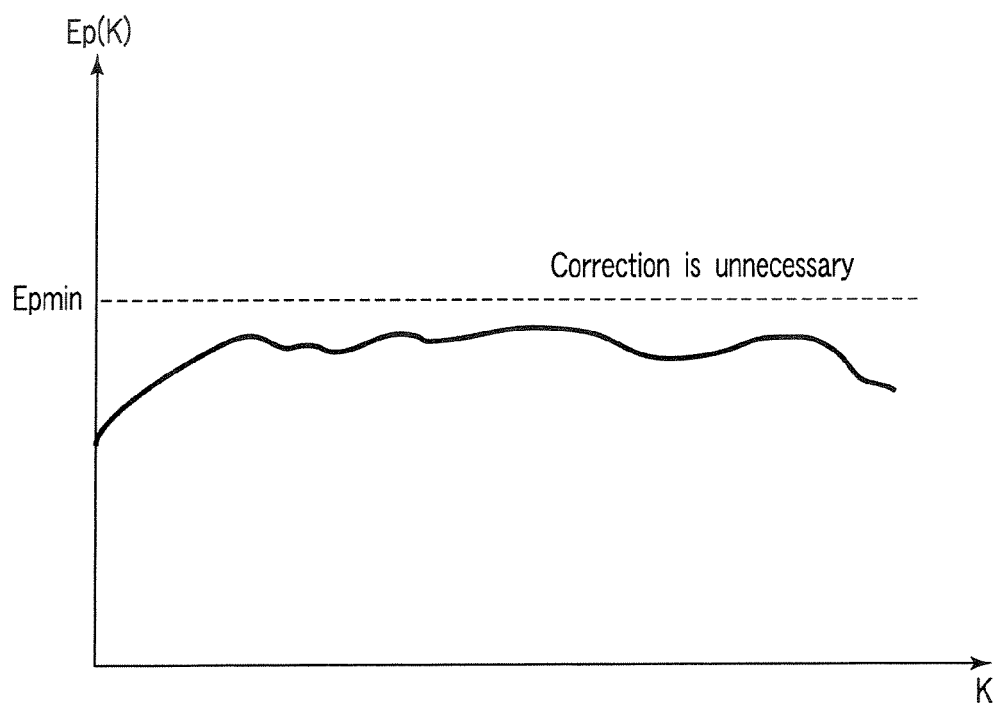
FIG. 10B is a graph showing an artifact frequency profile Fp(k) in this embodiment.

The following is a case wherein (M+1) images are acquired, and subtraction images are displayed with one of the acquired images being set as a mask image and the M images being set as contrast images. In this case, the mask image is a frame set by default. In general, the first frame is set as a mask image. First of all, the program obtains an artifact intensity Ep(k) and an artifact frequency Fp(k) for each frame by using the M subtraction images. The program performs a threshold process with respect to each of Epmin and Fpmin for the obtained calculated values. The program determines that pixel shifting is required for a frame which exceeds at least one of the thresholds (FIGS. 10A and 10B explain a case wherein only an artifact intensity is used). In this case, the program determines by using both the artifact intensity and the artifact frequency whether pixel shifting is required. However, the necessity/unnecessity of pixel shifting may be determined by using one of them.

If there is at least one frame for which the necessity of pixel shifting is determined, processing is performed in the same manner as in the second modification. However, this processing is performed for only a frame for which necessity of pixel shifting is determined. If there is no frame for which necessity of pixel shifting is determined, the processing is not performed. During the processing, the automatic button is set in the depressed state, and the execution, cancellation, and application buttons are set in the gray-out state. After the completion of the processing, the execution, cancellation, and application buttons return to the initial states. When the observer determines that the processing result is proper, and presses the execution button, the processing is confirmed, and a pixel shift amount is registered. As a result, the automatic button returns to the initial state. The subsequent display operation is performed by using the calculated pixel shift amount. If the processing is not required, the automatic button automatically returns to the initial state.

(10th Modification)

According to the above description, the processing is automatically applied. However, it suffices to provide a semi-automatic switch for determining during the execution of the radiography program whether to automatically perform pixel shifting and make the observer determine the necessity/unnecessity of correction. In this case, the necessity/unnecessity of correction is determined by the automatic method described in the second and third embodiment (modification), and the processing is executed in the background. However, the observer determines whether to apply this. More specifically, the automatic button in the pixel shift column is set in the initial projected state, and the same processing as that in the third modification is executed in the background up to the identification of a pixel shift amount (pixel shifting and subtraction are not executed). When the observer pressed the automatic button, the control unit 11 executes pixel shifting and subtraction on the basis of the results calculated so far. The operator confirms the processing by using the execution button.

(12th Modification)

According to the above description, pixel shifting is automatically performed. However, at a frame for which the observer has executed pixel shifting by operating the manual button and semi-automatic button, the processing for this frame is omitted from the automatic processing, and priority is given to the processing result determined by the observer.

Note that the present invention is not limited to the above embodiments, and constituent elements can be variously modified and embodied at the execution stage within the spirit and scope of the invention. Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image diagnostic apparatus comprising:
a radiography unit which generates a mask image before injection of a contrast medium and a plurality of contrast images after injection of the contrast medium by radiographing a subject before and after injection of the contrast medium;
an image storage unit which stores the mask image and the plurality of contrast images;
a region setting unit which sets a region of interest in a subtraction image from the mask image and the plurality of contrast images;
a pixel shift amount detecting unit which detects a pixel shift amount between the mask image and the plurality of contrast images upon localization to the set region of interest, wherein the pixel shift amount detecting unit detects a pixel shift amount for each of the plurality of contrast images, or detects a pixel shift amount common to the plurality of contrast images; and
a pixel shift processing unit which shifts at least one of the mask image and the plurality of contrast images in accordance with the detected pixel shift amount and performs subtraction between the images,
wherein the region setting unit sets, as the region of interest, a motion artifact occurrence region remaining in a subtraction image between the mask image and the plurality of contrast images.

2. An apparatus according to claim 1, wherein the region setting unit sets, as the motion artifact occurrence region, a region appearing with reverse polarity to the contrast medium on the subtraction image.

3. An apparatus according to claim 2, wherein the region setting unit removes a portion of the set motion artifact occurrence region which corresponds to a vertex direction and a lateral direction.

4. An apparatus according to claim 2, wherein the region setting unit includes
means for calculating a pixel value total sum of pixels appearing with the reverse polarity, for each pixel, with respect to a plurality of subtraction images between the mask image and the plurality of contrast images, and
means for setting, as the region of interest, a region set from a distribution of the pixel value total sums by a threshold process.

5. An apparatus according to claim 2, wherein the region setting unit comprises
means for specifying a maximum absolute value of pixels appearing with the reverse polarity, for each pixel, with respect to a plurality of subtraction images between the mask image and the plurality of contrast images, and
means for setting, as the region of interest, a region set from a distribution of the maximum absolute values by a threshold process.

6. An apparatus according to claim 2, wherein the region setting unit comprises means for calculating, for each pixel, a frequency at which a pixel value of a pixel appearing with the reverse polarity exceeds a first threshold with respect to a plurality of subtraction images between the mask image and the plurality of contrast images, and means for setting, as the region of interest, a region set from a distribution of the frequencies by a threshold process using a second threshold.

7. An apparatus according to claim 2, wherein the region setting unit includes means for expanding the region set by the threshold process by a predetermined distance or with a predetermined ratio.

8. An apparatus according to claim 2, wherein the region setting unit includes means for removing a predetermined range from the region set by the threshold process.

9. An apparatus according to claim 1, wherein the region setting unit sets, as the region of interest, a non contrast region other than a contrast region identified from a subtraction image between the mask image and the plurality of contrast images.

10. An apparatus according to claim 9, wherein the region setting unit includes means for calculating a pixel value total sum of pixels appearing with the same polarity as that of a contrast medium, for each pixel, with respect to a plurality of subtraction images between the mask image and the plurality of contrast images, and means for setting, as the region of interest, a region set from a distribution of the pixel value total sums by a threshold process.

11. An apparatus according to claim 9, wherein the region setting unit comprises means for specifying a maximum absolute value of pixels appearing with the same polarity as that of a contrast medium, for each pixel, with respect to a plurality of subtraction images between the mask image and the plurality of contrast images, and means for setting, as the region of interest, a region set from a distribution of the maximum absolute values by a threshold process.

12. An apparatus according to claim 9, wherein the region setting unit comprises means for calculating, for each pixel, a frequency at which a pixel value of a pixel appearing with the same polarity as that of a contrast medium exceeds a first threshold with respect to a plurality of subtraction images between the mask image and the plurality of contrast images, and means for setting, as the region of interest, a region set from a distribution of the frequencies by a threshold process using a second threshold.

13. An apparatus according to claim 1, wherein the region setting unit sets, as the region of interest, a region obtained by removing a contrast region identified by a subtraction image between the mask image and the plurality of contrast images from a motion artifact occurrence region identified from the subtraction image.

14. An apparatus according to claim 1, wherein the region setting unit sets the region of interest in a region including at least part of a skull base.

15. An apparatus according to claim 1, wherein the pixel shift amount detecting unit includes frame group sorting means for sorting said plurality of contrast images into a plurality of frame groups, and pixel shift amount detecting means for detecting a pixel shift amount for each of the frame groups.

16. An apparatus according to claim 15, wherein the frame group sorting means includes means for calculating a pixel value total sum of pixels appearing with reverse polarity to the contrast medium for each of a plurality of subtraction images between the mask image and the plurality of contrast images, and means for determining a sorting position for the frame groups from a change in the pixel value total sum.

17. An apparatus according to claim 15, wherein the frame group sorting means includes means for calculating the number of pixels which appear with reverse polarity to the contrast medium and exceed a first threshold for each of a plurality of subtraction images between the mask image and the plurality of contrast images, and means for determining a sorting position for the frame groups from a change in the number of pixels.

18. An apparatus according to claim 15, wherein when the frame group sorting means determines frames ranging from an Lth frame to an Nth frame as a first frame group from said plurality of subtraction image, the pixel shift amount detecting means calculates a pixel value total sum for each of the subtraction images from the Lth frame to the Nth frame, specifies a frame having a pixel value total sum nearest to an average or median of the pixel value total sums, and identifies a pixel amount identified between a contrast image corresponding to the specified frame and the mask image commonly to each of the contrast images from the Lth frame to the Nth frame.

19. An apparatus according to claim 18, wherein the determination unit includes means for calculating a pixel value total sum of pixels appearing with reverse polarity to the contrast medium with respect to each of a plurality of subtraction images between the mask image and the plurality of contrast images, and means for specifying a contrast image which requires the pixel shift processing in accordance with a result of comparison between the pixel value total sum and a predetermined threshold.

20. An apparatus according to claim 15, wherein the pixel shift amount detecting means includes means for calculating a difference between a total sum of pixel values appearing with reverse polarity on a subtraction image of an Lth frame and a total sum of pixel values appearing with reverse polarity on a subtraction image of a frame following the Lth frame, when it is determined that an image of an (L−1)th frame and an image of the Lth frame are delimiters of frame groups, and means for, when a frame at which the difference exceeds a predetermined threshold is an Nth frame, identifying a pixel shift amount identified by the plurality of contrast images of the Lth frame commonly to the plurality of contrast images from the Lth frame to an (N−1)th frame.

21. An apparatus according to claim 1, further comprising a determination unit which determines necessity/unnecessity of pixel shift processing for each of the plurality of contrast images.

22. An apparatus according to claim 21, wherein the determination unit includes means for calculating, for each pixel, a frequency at which a pixel value of a pixel appearing with reverse polarity to the contrast medium exceeds a first threshold for each of a plurality of subtraction image between the mask image and the plurality of contrast images, and means for specifying a contrast image which requires the pixel shift processing in accordance with a result of comparison between the frequency and a second threshold.

23. An apparatus according to claim 21, wherein the determination unit includes
   means for calculating a pixel value total sum of pixels appearing with reverse polarity to the contrast medium with respect to each of a plurality of subtraction images between the mask image and the plurality of contrast images,
   means for calculating, for each pixel, a frequency at which a pixel value of a pixel appearing with the reverse polarity exceeds a first threshold with respect to each of said plurality of subtraction images, and
   means for specifying a contrast image which requires the pixel shift processing in accordance with a result of comparison between the pixel value total sum and a second threshold and a result of comparison between the frequency and a third threshold.

24. An image diagnostic apparatus comprising:
   an image storage unit which stores a mask image before injection of a contrast medium and a plurality of contrast images after injection of the contrast medium generated by radiographing a subject before and after injection of the contrast medium;
   a region setting unit which sets a region of interest in a subtraction image from the mask image and the plurality of contrast images;
   a pixel shift amount detecting unit which detects a pixel shift amount between the mask image and the plurality of contrast images upon localization to the set region of interest, wherein the pixel shift amount detecting unit detects a pixel shift amount for each of the plurality of contrast images, or detects a pixel shift amount common to the plurality of contrast images; and
   a subtraction processing unit which shifts at least one of the mask image and the plurality of contrast images in accordance with the detected pixel shift amount and performs subtraction between the images,
   wherein the region setting unit sets, as the region of interest, a motion artifact occurrence region remaining in a subtraction image between the mask image and the plurality of contrast images.

\* \* \* \* \*